United States Patent
Pesach et al.

(10) Patent No.: US 7,646,484 B2
(45) Date of Patent: Jan. 12, 2010

(54) METHOD AND APPARATUS FOR PERFORMING OPTICAL MEASUREMENTS OF A MATERIAL

(75) Inventors: Benny Pesach, Rosh-Ha'ayin (IL); Gabriel Bitton, Jerusalem (IL); Ron Nagar, Tel-Aviv (IL)

(73) Assignee: Intellidx, Inc., Santa Clara, CA (US)

( * ) Notice: Subject to any disclaimer, the term of this patent is extended or adjusted under 35 U.S.C. 154(b) by 261 days.

(21) Appl. No.: 11/355,434

(22) Filed: Feb. 16, 2006

(65) Prior Publication Data

US 2007/0052965 A1    Mar. 8, 2007

Related U.S. Application Data

(63) Continuation-in-part of application No. 10/491,505, filed as application No. PCT/IL02/00813 on Oct. 7, 2002, now abandoned.

(51) Int. Cl.
*G01N 21/00* (2006.01)
(52) U.S. Cl. .................. 356/432; 356/39; 356/246; 356/442
(58) Field of Classification Search .............. 356/39, 356/40–442
See application file for complete search history.

(56) References Cited

U.S. PATENT DOCUMENTS

| | | | |
|---|---|---|---|
| 2,554,321 A | 5/1951 | Bray | |
| 4,051,372 A | 9/1977 | Aine | |
| 4,091,681 A | 5/1978 | Hordvik | |
| 4,276,780 A | 7/1981 | Patel et al. | |
| 4,303,343 A | 12/1981 | Patel et al. | |
| 4,385,634 A | 5/1983 | Bowen | |
| 4,429,999 A | 2/1984 | Bimberg et al. | |
| 4,682,897 A | 7/1987 | Saito et al. | |
| 4,805,623 A * | 2/1989 | Jobsis | 356/320 |
| 5,048,969 A | 9/1991 | Deason et al. | |
| 5,159,411 A | 10/1992 | Hammerich et al. | |
| 5,444,541 A | 8/1995 | Small et al. | |
| 5,452,716 A | 9/1995 | Clift | |
| 6,014,204 A | 1/2000 | Prahl et al. | |
| 6,049,728 A | 4/2000 | Chou | |
| 6,108,096 A * | 8/2000 | Ushio et al. | 356/432 |
| 6,188,476 B1 | 2/2001 | Hafeman et al. | |
| 6,846,288 B2 | 1/2005 | Nagar et al. | |
| 6,958,809 B2 | 10/2005 | Sterling et al. | |
| 0,250,217 A1 | 11/2005 | Keenan et al. | |

(Continued)

FOREIGN PATENT DOCUMENTS

GB    2322941    9/1998

(Continued)

OTHER PUBLICATIONS

Bunimovich et al. "Measurements of Absorption Coefficients Using Noncontact Fiber-Optic Laser Calorimetry", Applied Optics, 34(4): 743-745, 1995. Fig.3.

(Continued)

*Primary Examiner*—Gregory J Toatley, Jr.
*Assistant Examiner*—Iyabo S Alli
(74) *Attorney, Agent, or Firm*—Mintz, Levin, Cohn, Ferris, Glovsky and Popeo P.C.; Ivor R. Elrifi; Matthew Pavao

(57) ABSTRACT

A method of determining an optical parameter or function thereof for a liquid, the method comprising: flowing the liquid through a flow cell; transmitting a pulse of light into the liquid in the flow cell; generating a signal responsive to energy that the material emits responsive to a portion of the light from the light pulse that is absorbed by the liquid; and using the signal to determine the optical parameter or function thereof.

11 Claims, 3 Drawing Sheets

U.S. PATENT DOCUMENTS

| | | |
|---|---|---|
| 7,001,353 B2 * | 2/2006 | Bosetto et al. ............... 422/44 |
| 7,050,157 B2 | 5/2006 | Braig et al. |
| 7,061,593 B2 | 6/2006 | Braig et al. |
| 7,271,912 B2 | 9/2007 | Sterling et al. |
| 7,364,562 B2 | 4/2008 | Braig et al. |
| 7,388,202 B2 | 6/2008 | Sterling et al. |
| 7,480,032 B2 | 1/2009 | Braig et al. |
| 7,481,787 B2 | 1/2009 | Gable et al. |
| 2002/0155615 A1 | 10/2002 | Novikov et al. |
| 2003/0108976 A1 | 6/2003 | Braig et al. |
| 2004/0054268 A1 | 3/2004 | Esenaliev et al. |
| 2004/0127777 A1 | 7/2004 | Ruchti et al. |
| 2005/0105095 A1 | 5/2005 | Pesach et al. |
| 2005/0106749 A1 | 5/2005 | Braig et al. |
| 2006/0009727 A1 | 1/2006 | O'Mahony et al. |
| 2007/0060872 A1 | 3/2007 | Hall et al. |
| 2007/0225675 A1 | 9/2007 | Ries et al. |
| 2007/0240497 A1 | 10/2007 | Ries et al. |
| 2007/0244381 A1 | 10/2007 | Ries et al. |
| 2007/0244382 A1 | 10/2007 | Ries et al. |

FOREIGN PATENT DOCUMENTS

| | | |
|---|---|---|
| JP | 59-182338 | 10/1984 |
| JP | 09-145683 | 6/1997 |
| WO | WO 98/14118 | 4/1998 |
| WO | WO 98/38904 | 9/1998 |
| WO | WO 02/15776 | 2/2002 |
| WO | WO 2005/111634 | 11/2005 |

OTHER PUBLICATIONS

Hoelen et al. "A New Theoretical Approach to Photoacoustic Signal Generation", Journal of the Acoustical Society of America, 106(2): 695-706, 1999. Abstract.

Lai et al. "Theory of the Pulsed Optoacoustic Technique", Journal of the Acoustical Society of America, 72(6): 2000-2007, 1982. Abstract.

MacKenzie et al. "Advances in Photoacoustic Noninvasive Glucose Testing", Clinical Chemistry, 45(9): 1587-1595, 1999. http://www.clinchem.org/cgi/content/full/45/9/1587.

Oraevsky et al. "Determination of Tissue Optical Properties by Piezoelectric Detection of Laser-Induced Stress Waves", SPIE, Laser-Tissue Interaction, 1882: 86-98, 1993.

* cited by examiner

METHOD AND APPARATUS FOR PERFORMING OPTICAL MEASUREMENTS OF A MATERIAL

RELATED APPLICATIONS

The present application is a continuation in part of U.S. patent application Ser. No. 10/491,505 filed Mar. 31, 2004 which is a national phase application of PCT Application PCT/IL02/00813 filed Oct. 7, 2002.

FIELD OF THE INVENTION

The invention relates to determining absorption of electromagnetic radiation by a material and in particular absorption of light by a material.

BACKGROUND OF THE INVENTION

It is well known to assay components of a material by measuring absorption coefficients of the material for light at suitable wavelengths. A component of a material contributes to an absorption coefficient of the material for light at a given wavelength in proportion to $\sigma\rho$ where $\rho$ is a concentration of the component and $\sigma$ is an absorption cross-section of the component for light at the given wavelength.

To determine an absorption coefficient of a material for light at a given wavelength, generally, a sample of the material is illuminated with light at the given wavelength. An amount of the light that is transmitted through the sample is measured to determine attenuation that the light suffers in passing through the sample and the Beer-Lambert law is then used to determine the absorption coefficient. If $\alpha$ represents the absorption coefficient and L the optical path-length of the light through the material, then by the Beer-Lambert law $I = I_o \exp(-\alpha L)$, where I is the intensity of light transmitted through the material and $I_o$ is the intensity of light incident on the material.

Generally $\alpha$ is a function of concentration of a plurality of different components in the material. In order to determine concentration of a particular component of the material, $\alpha$ is measured at a plurality of different wavelengths. The concentration of a particular component of the material is determined from known absorption cross-sections of components of the material and the measurements of the absorption coefficient at the different wavelengths. U.S. Pat. No. 5,452,716 to V. Clift, the disclosure of which is incorporated herein by reference, describes measuring absorption coefficients for blood at a plurality of wavelengths to assay blood glucose.

Numerous devices, hereinafter referred to as "photometers", of various designs are available for measuring an absorption coefficient of a material. The devices comprise a suitable light source, such as a laser or LED, which provides a beam of light that is passed through a sample of a material to be tested. Intensity of the provided beam of light is measured to provide a value of $I_o$ and a measurement of intensity of light transmitted through the sample provides a value for I. A value for an optical path-length L of the beam of light through the sample is generally determined from a shape of the sample, or in the case of a liquid, often from a shape of a cuvette that contains the liquid.

In some photometers, referred to as "vertical-beam photometers", that are used to determine absorption coefficients of a liquid, a sample of the liquid is held in an open receptacle. A beam of light is transmitted "vertically" through the open end of the receptacle, the liquid contained in the receptacle and the bottom of the receptacle to determine attenuation of the beam and thereby an absorption coefficient of the liquid. The optical path-length L of the light beam through the liquid is determined by the height to which the receptacle is filled with the liquid and a shape of a meniscus formed at an interface of the liquid with the air.

In general, both the height of a liquid sample in a receptacle of a vertical-beam photometer and the shape of its meniscus cannot be controlled to an accuracy with which dimensions of a cuvette can be controlled. As a result, optical path-lengths of light through liquid samples in a vertical-beam photometer are generally not as accurately known or controllable as optical path-lengths through samples in a photometer for which optical path-lengths are determined by dimensions of a cuvette. Measurements of absorption coefficients provided by vertical-beam photometers are therefore generally not as accurate as measurements of absorption coefficients provided by other types of photometers.

However, vertical-beam photometers are popular because they enable rapid sampling of large numbers of liquid samples. The receptacles that hold liquid samples to be tested are generally formed as small wells in "trays" produced from a suitable material. The wells in a tray are easily and quickly filled with liquids to be tested. Once filled, the tray is rapidly positioned to expose the liquid in each of the wells to a beam of light that the photometer provides for measuring absorption coefficients.

U.S. Pat. No. 6,188,476, the disclosure of which is incorporated herein by reference, discusses the problem of determining optical path-lengths of liquid samples whose absorption coefficients are measured using vertical beam photometry. The patent describes methods for determining optical path-lengths of the sample solutions using calibration measurements of path-lengths at two different wavelengths for various common solvents that the liquid samples might contain.

In addition to errors in absorption coefficient measurements generated by errors in determination of optical path-lengths L, absorption coefficient measurements provided by photometers are often subject to error resulting from variations in intensity of light $I_o$ provided by the light source and drift in sensitivity of a detector used to determine I.

In medical applications, a "medical" photometer is used to measure absorption of light by a patient's blood at various wavelengths, optionally to provide an assay of a component, such as glucose, in the blood. Often the medical photometer is configured to draw blood from the patient or to receive blood from a system, such as for example, a heart lung machine, through which the patient's blood is flowing and shunt the blood through a flow cell. The medical photometer illuminates the blood in the flow cell with light at a suitable wavelength or wavelengths and determines how much of the light is transmitted through the flow cell to acquire absorption measurements for the blood at the wavelength or wavelengths.

However, for many medical purposes, it is desired to acquire absorption measurements in blood for light at the mid infra-red wavelength range. For these wavelengths of light, blood is a relatively strong optical absorber and light transmitted into a flow cell through which blood is flowing is strongly attenuated with distance that the light propagates in the blood. In order for a sufficient amount of light to pass through the flow cell so that reliable absorption measurements for the blood can be acquired, the flow cell must generally be made relatively small in a region through which the light is transmitted to acquire the absorption measurements. Often, a flow cell-cross-section at a location at which absorption measurements of blood are made is so small that the path length of light through the blood at the location is only about 20 microns in length. For flow cells comprising a region having a cross-section with such a small dimension, blood has a tendency to clot in the region and not only block the flow cell but generate a possible threat to a patient's health.

SUMMARY OF THE INVENTION

An aspect of some embodiments of the present invention relates to providing an improved photometer for determining an absorption coefficient, or function of the absorption coefficient, for light of a sample of a material. Hereinafter, the term absorption coefficient is used generically to include a function of the absorption coefficient.

An aspect of some embodiments of the present invention relates to providing a photometer that determines an optical path-length for a beam of light that is transmitted through a sample of a material to determine a value for an absorption coefficient of the material.

An aspect of some embodiments of the invention relates to providing a photometer that provides a measurement of an absorption coefficient of a sample that is substantially independent of variations in intensity of a light beam which is transmitted through the sample to determine the coefficient.

According to an aspect of some embodiments of the present invention, the value of the absorption coefficient is substantially unaffected by drift in sensitivity of a detector used to determine intensity of light in the light beam that is transmitted through a sample.

A photometer, in accordance with an embodiment of the present invention comprises a light source and an energy detector. The energy detector generates a signal responsive to energy incident thereon from which signal an amount of the incident energy can be determined.

The energy detector is coupled to a sample of a material for which an absorption coefficient is to be determined and the light source is controlled to provide at least one pulse of light that is transmitted into the sample. Some of the light in a light pulse that is transmitted into the sample is absorbed by the material and some of the light in the light pulse is not absorbed by the material. The light source and the energy detector are positioned so that at least a portion of light in the light pulse that is not absorbed by the material reaches the energy detector as a pulse of optical energy, either directly from the light source or by reflection from the material. (i.e. in some embodiments of the present invention, the pulse of optical energy reaches the detector along a direct path through the material from the light source to the detector. In some embodiments of the present invention, the pulse of optical energy reaches the detector after reflection by the material.)

The pulse of optical energy, hereinafter referred to as "immediate energy", from the non-absorbed light reaches the detector following a generally very short delay that is determined by a distance that the light travels from the light source to the detector divided by the speed of light. In response to the immediate energy, the detector generates a signal, hereinafter referred to as an "immediate signal", from which signal the intensity and amount of immediate energy incident on the detector are, optionally, determined using methods known in the art.

Energy from light in the light pulse that is absorbed by the material is subsequently released and a portion of the released energy, hereinafter referred to as "delayed energy", reaches the energy detector after the immediate energy reaches the detector. A time period between the arrival of the immediate energy at the detector and arrival of the delayed energy at the detector is hereinafter referred to as an "absorption delay".

The absorption delay is a sum of a "propagation delay" and a "release delay". Generally, the delayed energy propagates to the energy detector from a point in the material at which the energy is released as an acoustic wave or as heat propagated by convection. A difference between the speed of light and speed of sound or thermal convection in the material causes the propagation delay. The release delay is a time between a time at which light is absorbed by the material and a time at which energy absorbed from the light is released by the material. Generally, the propagation delay is much longer than the release delay and the absorption delay is dominated by the propagation delay.

The energy detector generates a signal, hereinafter referred to as a "delayed signal", in response to an amount of delayed energy that reaches the detector. As in the case of the immediate signal, intensity and an amount of delayed energy incident on the detector are, optionally, determined from the delayed signal.

In some embodiments of the present invention, the energy detector comprises an acoustic detector. Immediate energy reaches the acoustic detector in the form of a pulse of optical energy from light in the light pulse that is not absorbed by the material and generates an acoustic pulse in the acoustic detector, responsive to which the detector generates the immediate signal. Light from the light pulse that is absorbed by the material generates sound waves, "photoacoustic waves", in the material by a photoacoustic process. The sound waves propagate to the acoustic detector and transport "delayed energy" to the detector, responsive to which the detector generates the delayed signal.

Generation of acoustic waves by the photoacoustic effect is discussed in U.S. Pat. No. 6,846,288 the disclosure of which is incorporated herein by reference. The relationship between the amplitude of a photoacoustic wave and an amount of energy absorbed by a region of tissue that generates the photoacoustic wave is described in U.S. Pat. No. 4,385,634 to Bowen and PCT publication WO 98/14118 the disclosures of which are incorporated herein by reference. Expressions for amplitude of a photoacoustic wave are also given in an article by Lai, H. M. and Young, K. J. in Acoust. Soc. Am. Vol 76, pg 2000 (1982), in an article by MacKenzie et al., "Advances in Photoacoustic Noninvasive Glucose Testing", Clin. Chem. Vol 45, pp 1587-1595 (1999) and in an article by C. G. A. Hoelen et al., "A New Theoretical Approach to Photoacoustic Signal Generation", Acoust. Soc. Am. 106 2 (1999) the disclosures of all of which are incorporated herein by reference.

The immediate and delayed energies are proportional respectively to the amount of light from the light pulse that is not absorbed by the material during transit of the light pulse through the material and the amount of light that is absorbed by the material during transit of the light pulse through the material. In accordance with an embodiment of the present invention, the immediate and delayed signals are processed to provide a ratio, hereinafter an "absorption ratio", between the amount of light absorbed from the light pulse and the amount of light that is not absorbed from the light pulse. Since both the absorbed and non-absorbed amounts of light are proportional to the intensity of light in the light pulse, the absorption ratio is substantially independent of intensity of light in the light pulse. The absorption ratio is a function substantially only of an absorption coefficient of the material for light in the light pulse and a path-length of the light pulse through the sample. In accordance with an embodiment of the present invention, the absorption ratio is used to determine the absorption coefficient.

The absorption ratio is a particularly sensitive measure of the absorption coefficient since the absorption ratio generally exhibits a greater relative change for a same change in absorption coefficient than either the amount of energy absorbed or not absorbed by the material from the light pulse. The absorption ratio is also substantially independent of intensity of light in the light pulse. Furthermore, since in accordance with an embodiment of the present invention, a same energy detector senses and generates signals responsive to both the immediate and delayed energies, the absorption ratio is substantially independent of changes in sensitivity of the detector.

It is noted that in prior art photometers, two detectors are generally used to determine an absorption coefficient of a sample of a material. One of the detectors measures intensity "$I_o$" of light transmitted by a light source into the sample and a second detector measures intensity of light "I" that is transmitted through the sample. Changes in relative sensitivity of the two detectors or in an optical system that directs a portion of the light from the light source to the first detector and a portion to the sample are sources of error that can compromise accuracy of a measurement provided by such a prior art photometer. A photometer, in accordance with an embodiment of the present invention is substantially independent of such sources of error. A photometer, in accordance with an embodiment of the present invention therefore generally provides a particularly robust and sensitive measure of absorption coefficient.

For embodiments of the present invention for which the detector is an acoustic detector a portion of the acoustic energy repeatedly bounces back and forth between the detector and a surface of the sample. The speed of sound in the sample and frequency with which energy bounces back and forth between the detector and the surface is used, in accordance with an embodiment of the invention, to determine a distance between the detector and the surface and thereby a path-length for light through the sample.

In some embodiments of the present invention, a value for the speed of sound in the sample used to determine a distance between the detector and the surface is experimentally determined from a time it takes for sound to travel a known distance through the sample. For example, if the sample is a liquid contained in a cuvette, the speed of sound can be determined by positioning a suitable acoustic transducer on a side of the cuvette below a level of the liquid in the cuvette. The transducer is used to measure a time it takes sound to travel back and forth in the liquid between sides of the cuvette. Since the dimensions of the cuvette are known, the speed of sound in the liquid can be determined.

For a material sample having a thickness substantially greater than an inverse of an absorption coefficient of the material, a photometer, in accordance with some embodiments of the invention, operates to determine the absorption coefficient without need to determine, or to directly determine, an optical path-length in the material for light that is used to determine the absorption coefficient. In such photometers, both a light source and detectors are optionally located on a same side of a cuvette or suitable flow cell that contains the material and there is in general no need to measure an amount of light that is transmitted through the sample. Expressions for immediate and delayed energy that are independent of path length are determined and used to provide an absorption coefficient for the light. In some embodiments of the invention, the amplitude, and/or slope, and/or temporal shape of signals generated responsive to immediate and delayed energy are used to provide an absorption coefficient for the light.

Photometers in accordance with these types of embodiments of the invention are advantageously used as medical photometers. For example, as noted above, conventional medical photometers used for determining absorption coefficients of blood ex-vivo generally require a flow cell through which blood flows that is formed with a cross-section having at least one relatively small dimension along which dimension light is transmitted through the flow cell. Because of the relatively small cross-section dimension, these flow cells have a tendency to cause blood clotting that not only blocks the flow cells but may also generate a possible threat to a patient's health.

Using a medical photometer in accordance with an embodiment of the invention enables acquiring ex-vivo absorption measurements for blood using a "wide" flow cell whose cross-section is not limited by a relatively small dimension and one that therefore substantially reduces a probability of blood clotting. Optionally, a dimension of the internal cross-section of the flow cell along which dimension light is transmitted into the flow cell to acquire optical measurements of blood has a length that is greater than the absorption length of the light in the blood. Optionally the cross-section dimension is greater than two absorption lengths. Optionally, the cross-section dimension is greater than five absorption lengths. Optionally, the cross-section dimension is greater than ten absorption lengths.

It is noted that a "photoacoustic medical photometer" having a wide flow cell, in accordance with an embodiment of the invention, may determine an absorption coefficient for a tissue without recourse to a measure of immediate energy. Instead, an absorption coefficient is provided from a measurement of delayed energy and a measurement, optionally provided by a suitable detector, of intensity of light that generates the delayed energy in the tissue.

In some embodiments of the invention, a photoacoustic medical photometer determines an absorption and/or scattering coefficient for light in a sample tissue responsive to the slope and amplitude of signals generated responsive to photoacoustic waves that the photometer stimulates in the sample. Optionally, the signals are processed to determine the absorption and/or scattering coefficient using methods described in an article by A. A. Oraevsky et al entitled "Determination of Tissue Optical Properties by Piezoelectric Detection of Laser-Induced Stress Waves"; SPIE Vol. 1882 Laser-Tissue Interaction IV (1993); pp 86-98.

In some embodiments of the present invention, the detector comprises a thermal transducer. Direct energy that reaches the thermal transducer from light in the light pulse that is not absorbed by the material generates a change in temperature of the thermal transducer, responsive to which temperature change the detector generates the immediate signal. The detector generates the delayed signal responsive to thermal energy that reaches the detector, which is released by the material responsive to light absorbed by the material from the light pulse.

There is therefore provided in accordance with an embodiment of the invention, a method of determining an optical parameter or function thereof for a liquid, the method comprising: flowing the liquid through a flow cell; transmitting a pulse of light into the liquid in the flow cell; generating a signal responsive to energy that the material emits responsive to a portion of the light from the light pulse that is absorbed by the liquid; and using the signal to determine the optical parameter or function thereof.

Optionally, transmitting the light into the flow cell comprises transmitting the light in a direction along which the internal cross-section of the flow cell has a dimension that is greater than an absorption length of the light in the liquid.

In some embodiments of the invention, the liquid is blood. Optionally, the dimension is greater than two absorption lengths of the light in the blood. Optionally, the dimension is greater than five times the absorption length. Optionally, the dimension is greater than ten times the absorption length.

In some embodiments of the invention, the energy that the liquid emits is acoustic energy generated by a photoacoustic effect. In some embodiments of the invention, the energy that the liquid emits is thermal energy. In some embodiments of the invention, the liquid is blood.

In some embodiments of the invention, the method comprises generating a signal responsive to light from the light pulse that is scattered by the material and using the signal to determine the optical parameter or function thereof.

There is further provided in accordance with an embodiment of the invention, apparatus for determining an optical parameter or function thereof for a liquid, the apparatus comprising: a flow cell through which the liquid flows the flow cell having a cross-section dimension greater than an absorption length in the liquid for light for which the optical parameter or function thereof is determined; a light source that transmits a pulse of light into the liquid in the flow cell along the cross-section dimension; a detector that receives energy emitted by the material responsive to light from the light pulse that is absorbed by the material and generates a signal responsive to the received energy; and a processor that receives the signal and uses it to determine the optical parameter or function thereof.

Optionally, the dimension is greater than two absorption lengths of the light in the blood. Optionally, the dimension is greater than five times the absorption length. Optionally, the dimension is greater than ten times the absorption length.

In some embodiments of the invention, the energy that the liquid emits is acoustic energy generated by a photoacoustic effect. In some embodiments of the invention, the energy that the liquid emits is thermal energy. Optionally, the liquid is blood.

In some embodiments of the invention, the apparatus comprises a detector that receives light from the light pulse that is scattered by the material and generates a signal responsive thereto. Optionally, the processor receives the signal responsive to the scattered light and uses the signal to determine the optical parameter or function thereof.

There is further provided in accordance with an embodiment of the invention, apparatus for determining an optical parameter or function thereof for a liquid, the apparatus comprising: a flow cell through which the liquid flows; a light source that transmits a pulse of light into the liquid in the flow cell that generates photoacoustic waves in the liquid; a detector that receives energy from the photoacoustic waves and generates a signal responsive to the received energy; and a processor that receives the signal and uses it to determine the optical parameter or function thereof.

There is further provided in accordance with an embodiment of the invention, a method of determining an optical parameter or function thereof for a material, the method comprising: transmitting a pulse of light into the material; receiving energy that the material emits responsive to a portion of the light from the light pulse that is absorbed by the material; generating a signal responsive to the received energy; providing a model that relates the received energy to a distance that the light travels in the material; assuming a value for the distance; and determining the optical parameter or function thereof responsive to the first signal, the model and the assumed value.

Optionally, the assumed distance is substantially greater than an absorption length of the light in the material. Optionally, the assumed distance is infinite.

In some embodiments of the invention, the material is strongly absorbing at a wavelength that characterizes the light.

In some embodiments of the invention, the material is a liquid. Optionally, the liquid is blood.

Optionally, transmitting the light into the blood comprises containing the blood in a receptacle having an internal dimension along a direction in which the light pulse is introduced into the blood that is greater than an absorption length of the light in the blood.

Optionally, the internal dimension is greater than two absorption lengths of the light in the blood. Optionally, the internal dimension is greater than five times the absorption length. Optionally, the internal dimension is greater than ten times the absorption length.

In some embodiments of the invention, the receptacle is a flow cell and the blood is flowing through the flow cell.

In some embodiments of the invention, the material emits comprises a pulse of acoustic energy generated in the material by a photoacoustic effect and generating the first signal comprises sensing the acoustic energy and generating the first signal responsive thereto.

In some embodiments of the invention, the energy that the material emits comprises thermal energy and generating the first signal comprises sensing the thermal energy and generating the first signal responsive thereto.

In some embodiments of the invention, the energy that the material emits comprises optical energy luminesced by the material and generating the first signal comprises sensing the luminesced light and generating the first signal responsive thereto.

In some embodiments of the invention, the method comprises: receiving light scattered by the liquid from the light pulse; generating a signal responsive to the received scattered light; providing a model that relates the received scattered light to a distance that the light travels in the material; assuming a value for the distance; and determining the optical parameter or function thereof responsive to the signal, the model and the assumed value. Optionally, the optical parameter comprises an absorption coefficient for the light.

BRIEF DESCRIPTION OF FIGURES

Non-limiting examples of embodiments of the present invention are described below with reference to figures attached hereto. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale. The figures are listed below.

DETAILED DESCRIPTION OF EXEMPLARY EMBODIMENTS

Figure 1:
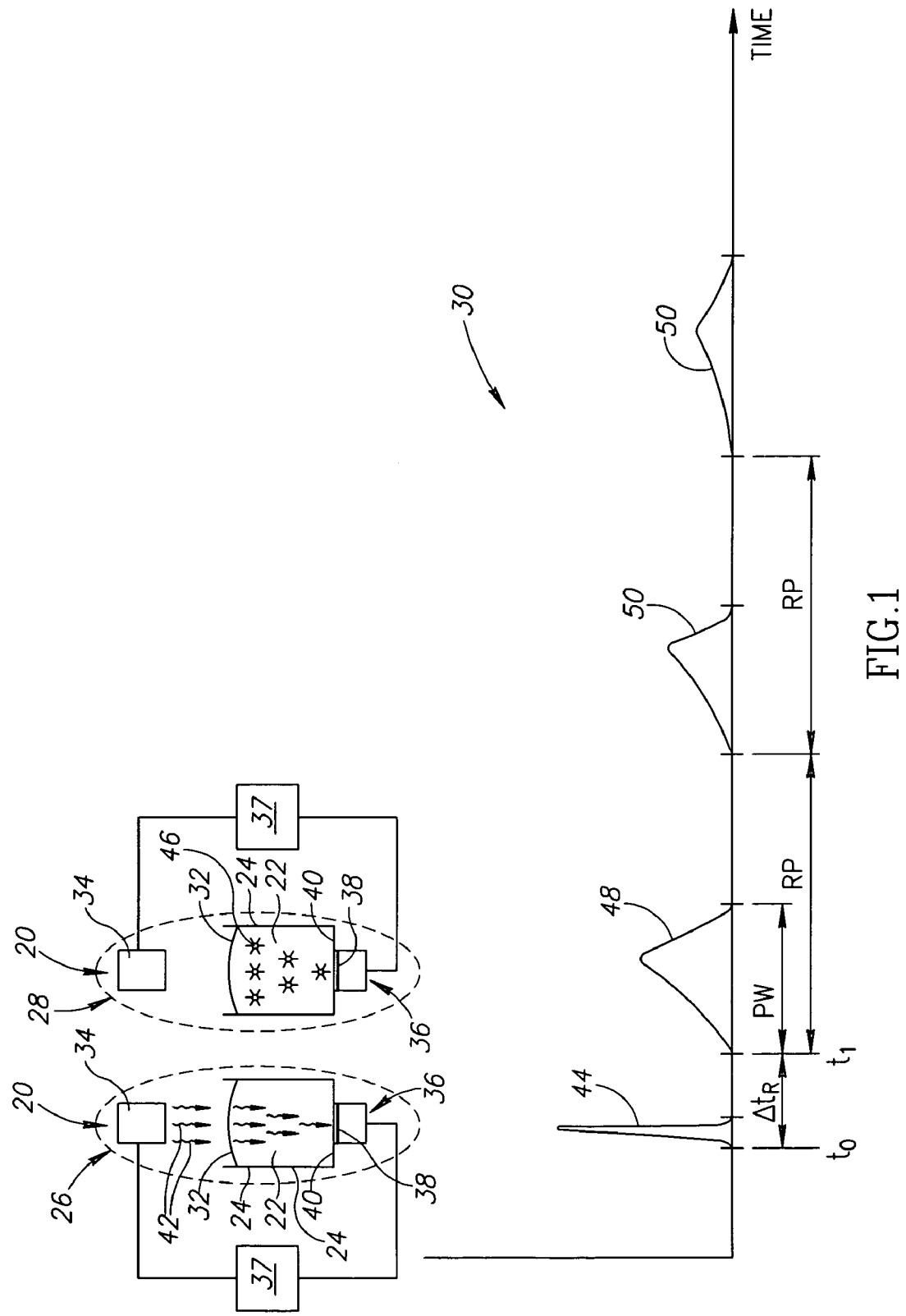
FIG. 1 schematically shows a vertical beam photometer determining an absorption coefficient of a liquid sample, in accordance with an embodiment of the present invention.

FIG. 1 schematically shows a vertical beam photometer 20, in accordance with an embodiment of the present invention, being used to determine an absorption coefficient for, by way of example, a sample of liquid 22 contained in a receptacle 24. Photometer 20 is shown at different times in the process of determining the absorption coefficient of liquid sample 22 in insets 26 and 28. A graph 30 schematically shows signals generated by photometer 20 as a function of time during the process. Liquid sample 22 has a meniscus 32 at a boundary between the liquid sample and the air. By way of example, in FIG. 1 meniscus 32 is shown as convex.

Photometer 20 comprises a light source 34, such as a laser, LED or arc lamp, an energy detector that is optionally an acoustic detector 36 and a controller 37. Acoustic detector 36 is optionally a piezoelectric detector. A surface 38 of detector 36 is preferably positioned in contiguous contact with a bottom 40 of receptacle 24, using methods known in the art. In inset 26, controller 37 controls light source 34 to illuminate liquid sample 22 with a pulse of light represented by wavy arrows 42.

Light in light pulse 42 that enters liquid 22 is attenuated by absorption in the liquid as the light pulse propagates in a direction towards acoustic detector 36. A decreasing number of wavy arrows 42 in a direction from light source 34 to detector 36 schematically indicate attenuation of the light pulse. A portion of the light in light pulse 42 is not absorbed by liquid 22, survives travel through liquid sample 22 and is incident on surface 38 of acoustic detector 36 as a relatively narrow pulse of "immediate optical energy". The pulse of immediate energy is schematically shown in graph 30 below inset 26 as a pulse 44. Pulse 44 begins at a time $t_o$ and has a pulse width substantially equal to the pulse width of light pulse 42.

An amount of immediate energy in pulse 44 is proportional to intensity $I_o$ of light in light pulse 42 that enters liquid 22. If the amount of immediate energy in pulse 44 is represented by "IE" then the immediate energy can be written $IE=\beta'I_o\exp(-\alpha D)$. In the expression for IE, D is a height of meniscus 32 above detector 36, and $\alpha$ is an absorption coefficient of liquid 22 for light in light pulse 42 and $\beta'$ is a constant of proportionality. $\beta'$ is substantially equal to the pulse width of light pulse 42 times a factor that is an efficiency of collection of non-absorbed light from light pulse 42. The efficiency factor is a function of the size of detector 36 and scattering of light in light pulse 42 as the light pulse travels through liquid 22. The efficiency factor can be calculated using a suitable model of a sample liquid and shape of receptacle 24 and/or determined experimentally. For example, it is noted that if detector 36 is relatively small, an amount of light that reaches the detector is relatively accurately described by $IE=\beta^*I_o\exp(-\alpha_E D)$ where $\beta^*$ is a proportionality constant and $\alpha_E$ is an attenuation or extinction coefficient for light in the material and is a function of both an absorption coefficient and a reduced scattering coefficient.

Immediate energy pulse 44 causes local heating of detector 36 in a region of surface 38 of the detector that produces sound waves in the detector. At a time substantially equal to time $t_o$, the detector generates an immediate signal responsive to the sound waves. The immediate signal is, via the sound waves, a function of IE and therefore of the amount of energy from light pulse 42 that is not absorbed by liquid 22. If "IS" represents the immediate signal, $I_o\exp(-\alpha D)$ may be written $I_o\exp(-\alpha D)=F(IS)$ where F represents a processing algorithm or functional relationship that is usable by controller 37 to determine $I_o\exp(-\alpha D)$ from the immediate signal IS.

In some embodiments of the present invention, a functional relationship between IS and $I_o\exp(-\alpha D)$ is linear. For example, in some embodiments of the present invention, amplitude of the immediate signal or amplitude of the signal integrated over time is a linear function of the incident immediate energy. For these embodiments of the present invention, if "AIS" represents the "linear" amplitude or time integrated amplitude of the immediate signal then AIS can be written $I_o\exp(-\alpha D)=\beta AIS$. In the expression for AIS, $\beta$ is a constant of proportionality, which includes a factor $1/\beta'$. (From the equation above that defines $\beta'$, immediate energy IE to $I_o\exp(-\alpha D) \cong IE/\beta'$). $\beta$ may be determined by appropriate calibration of photometer 20.

Light from light pulse 42 that is absorbed in liquid 22 deposits energy in the liquid that generates ultrasound waves by the photoacoustic effect. Sources of the ultrasound waves in liquid 22 are schematically shown as "starbursts" 46 in inset 28 of FIG. 1. Since intensity of light pulse 42 attenuates exponentially as the light pulse travels to detector 36, an amount of energy deposited in liquid 22 by the light pulse per unit volume of the liquid decreases exponentially with distance from meniscus 32. The decrease in deposited energy is schematically indicated by a decrease in the number of starbursts 46 shown in inset 28 in a direction from meniscus 32 to detector 36.

Ultrasound waves are generated at starbursts 46 following a short time delay, i.e. a "release delay" after energy is deposited by light pulse 42 at locations of the starbursts. Ultrasound waves that originate in a starburst 46 propagate away from the starburst at the speed of sound with substantially a same intensity in all directions from the starburst and are attenuated as they propagate in accordance with an acoustic absorption coefficient of liquid 22.

Some of the ultrasound waves propagate directly from a starburst 46 to detector 36 while some of the ultrasound waves reach detector 36 after bouncing around in the volume of liquid 22. Energy in the ultrasound waves that are incident on detector 36 is "delayed energy" that reaches the detector following transmission of light pulse 42 through liquid 22. Ultrasound energy that propagates directly from a starburst 46 located at a distance "d" from detector 36 reaches the detector after it is "released" from the starburst following a propagation time delay equal to about d/C where C is the speed of sound in the liquid sample. Ultrasound energy from the starburst 46 that does not travel directly from the starburst to detector 36, but instead bounces around in liquid 22 (off the walls of the container and the upper surface of the liquid) before reaching the detector, arrives at the detector after it is released following a propagation delay that is longer than d/C. The "indirect energy" from the starburst is also attenuated with respect to the direct energy due to the longer path traveled by the indirect energy in reaching detector 36 and reflective losses. As a result, generally, delayed ultrasound energy reaches detector 36 as a delayed acoustic energy pulse schematically represented by a pulse 48 in graph 30 that begins at a time $t_1$ following a time release delay "$\Delta t_R$" after time $t_o$. Release delay $\Delta t_R$ is a time that elapses from a time at which energy is absorbed by a region of liquid 22 to a time at which the region generates a photoacoustic wave responsive to the absorbed energy. Delayed energy pulse 48 has a maximum at a time about equal to the propagation time D/C following time $t_1$ and a pulse width "PW" indicated in graph 30, that is larger than D/C.

The time release delay is on the order of nanoseconds and is much shorter than the propagation delay, which is on the order of microseconds, that characterizes pulse 48. The time release delay can therefore generally be ignored in determining an absorption delay (i.e. time release delay plus propagation delay) that characterizes a time following $t_o$ at which delayed energy reaches detector 36. In FIG. 1 the size of time delay $\Delta t_R$ relative to the size of propagation delay D/C is greatly exaggerated for clarity of presentation. The total amount of ultrasonic energy incident on detector 36 during delayed energy pulse 48 is proportional to the total amount of energy absorbed by liquid 22. Let DE represent the total delayed energy incident on detector 36 during delayed energy pulse 48. Then $DE \cong \gamma'[I_o(1-\exp(-\alpha D))]$, where the expression in square brackets is equal to the total amount of energy absorbed from light pulse 42 by liquid 22 and $\gamma'$ is a constant of proportionality.

In response to delayed energy pulse 48, detector 36 generates a delayed signal "DS" having a functional relationship to DE and therefore to the amount of energy in light pulse 42 that is absorbed by liquid 22. Let the functional relationship between DS and the amount of energy in light pulse 42 that is absorbed by liquid 22 be represented by G(DS) so that $[I_o(1-\exp(-\alpha D))]=G(DS)$.

In some embodiments of the present invention, the amplitude or time integrated amplitude of the delayed signal is a linear function of DE. If the linear amplitude or time integrated amplitude of the delayed signal DS is represented by ADS, then ADS can be written $ADS \cong \gamma[I_o(1-\exp(-\alpha D))]$, where $\gamma$ is a constant of proportionality that includes a factor $1/\gamma'$. (From the definition of $\gamma'$, $I_o(1-\exp(-\alpha D)) \cong DE/\gamma'$).

In accordance with an embodiment of the present invention, a suitable processor, (not shown), which may be comprised in controller 37, determines a coefficient of absorption of liquid 22 from an absorption ratio "R", which is defined by the expression $R=G(DS)/F(IS)=[I_o(1-\exp(-\alpha D))]/[I_o \exp(-\alpha D)]=(1-\exp(-\alpha D))/\exp(-\alpha D)$. It is noted that the ratio R is more sensitive to changes in $\alpha$ than is the amount of energy from light pulse 42 that is absorbed by liquid 22 (and therefore of course also the amount of energy that is not absorbed by liquid 22). The relative change in R for a given change in $\alpha$ is greater than the relative change in the amount of energy absorbed or not absorbed from light pulse 42 for the given change in $\alpha$. R is therefore generally a relatively sensitive measure of $\alpha$. For embodiments of the present invention for which the immediate and delayed signals are "linear functions" of the immediate and delayed energies respectively, R is optionally determined from a ratio of the amplitudes or time integrated amplitudes of the immediate and delayed signals, i.e. $R=[\beta(ADS)]/[\gamma(AIS)]$.

It is seen from the above equation that R is independent of $I_o$. As a result, a determination of $\alpha$ using R is substantially independent of intensity of light pulse 42 and variations in output of light source 34. Furthermore, a delay between measurements of immediate and delayed energy is on the order of a transit time of sound through liquid sample 22. The transit time is typically a few microseconds long. During such a relatively short time period, changes in parameters that characterize and affect operation of components of photometer 20 are expected to be substantially negligible. As a result, measurements of a determined using photometer 20 are substantially immune to drift in these parameters.

In order to determine a from R, a value for the optical path-length D of light pulse 42 through liquid 22 is required. In some embodiments of the present invention D is determined using methods, such as for example a method described in U.S. Pat. No. 6,188,476 referenced above, available from prior art. In some embodiments of the present invention, photometer 20 optionally determines a value for D using acoustic energy pulses received by detector 36.

When delayed energy pulse 48 is incident on detector 36, not all of the acoustic energy in the pulse is deposited in the detector. A portion of the energy is reflected. The reflected energy propagates towards meniscus 32, where at the interface between the meniscus and the air a portion of the reflected energy is again reflected, this time back towards detector 36. The twice-reflected ultrasonic energy is incident on detector 36, where again a portion of the incident energy is reflected towards meniscus 32. Acoustic energy from delayed energy pulse 48 is thus repeatedly reflected back and forth between meniscus 32 and detector 36.

The repeatedly reflected energy is incident on detector 36 as a series of ultrasonic pulses 50, only two of which are shown, of decreasing amplitude. Pulses 50 have a repetition period "RP" that is about equal to 2D/C, which is a round trip time for sound to travel back and forth between detector 36 and meniscus 32. In accordance with an embodiment of the present invention, the series of reflected pulses 50 is analyzed by the processor using methods known in the art to determine a value for D. In some embodiments of the present invention, an ultrasound transducer (not shown) is positioned contiguous with a side wall of receptacle 24. The transducer is used to determine a transit time for sound back and forth between the side wall on which the transducer is positioned and another side wall of the receptacle. The transit time is used to determine a value for C.

Figure 2:
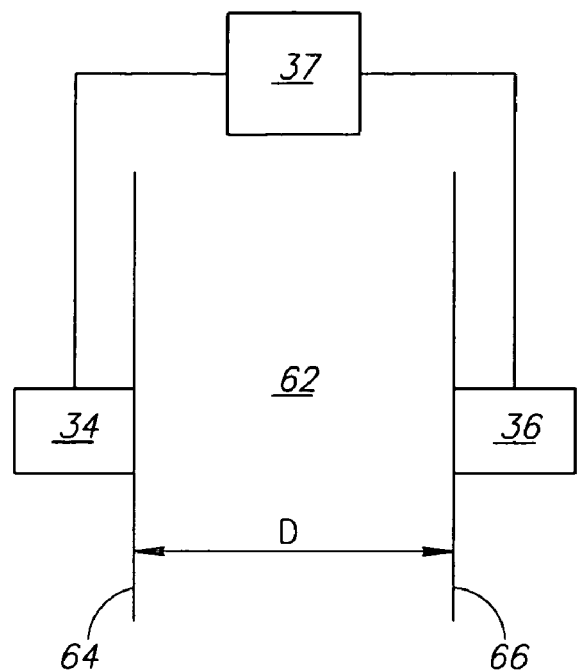
FIG. 2 schematically shows a photometer determining an absorption coefficient of a solid material, in accordance with an embodiment of the present invention.

FIG. 2 schematically shows another photometer 60 in accordance with an embodiment of the present invention. Photometer 60 is similar to photometer 20 but is not configured as a vertical beam photometer, and is shown by way of example determining an absorption coefficient of a sample of a solid material 62.

Photometer 60 operates similarly to photometer 20 and comprises components that are similar to the components comprised in photometer 20. When being used to determine an absorption coefficient of a solid, preferably light source 34 is contiguous with and optically coupled to a surface 64 of the solid. Energy detector 36 is preferably in contiguous contact with a surface 66 of material 62 opposite surface 64 to which light source 34 is coupled.

As in the case of photometer 20, controller 37 controls light source 34 to transmit a light pulse (not shown) into material 62. Detector 36 receives a pulse of immediate energy from light in the light pulse that is not absorbed by material 62 and generates an immediate signal IS responsive thereto. Subsequent to receiving a pulse of immediate energy, detector 36 receives a pulse of delayed energy generated by a photoacoustic effect caused by light in the light pulse that is absorbed by the material and generates a delayed signal DS responsive thereto. The immediate and delayed signals are optionally used to determine an absorption ratio from which an absorption coefficient of the material is determined.

In some embodiments of the present invention, a thickness "D" of material 62 that separates surfaces 64 and 66 is used to determine an optical path-length for the light pulse. In some embodiments of the present invention, acoustic energy pulses repeatedly reflected back and forth between surfaces 64 and 66 are used to determine a thickness for material 62 and thereby an optical path-length for the light pulse.

Whereas in FIG. 2 photometer 60 is shown determining an absorption coefficient for a solid material, photometer 60 may be used, in accordance with an embodiment of the present invention, to determine an absorption coefficient of a liquid. The liquid is placed in a suitable cuvette which is sandwiched between light source 34 and detector 36 similarly to the way in which solid material 62 is sandwiched between the light source and the detector as shown in FIG. 2. A light pulse is transmitted through the cuvette and the liquid it contains to generate immediate and delayed signals IS and DS that are used to determine an absorption coefficient for the liquid.

To remove effects of the cuvette on determination of the absorption coefficient of the liquid, a light pulse is transmitted through the cuvette when it is empty or filled with a liquid, such as water, having an accurately known absorption coefficient to provide calibration measurements of immediate and delayed signals. The calibration measurements are used to correct immediate and delayed signals generated by detector 36 from which the absorption coefficient of the liquid is determined. Assuming a distance between walls of the cuvette is known, a time between acoustic delayed energy pulses repeatedly reflected back and forth between the walls is used to determine a speed of sound in the liquid and the determined speed of sound is used to determine the absorption coefficient.

Figure 3:
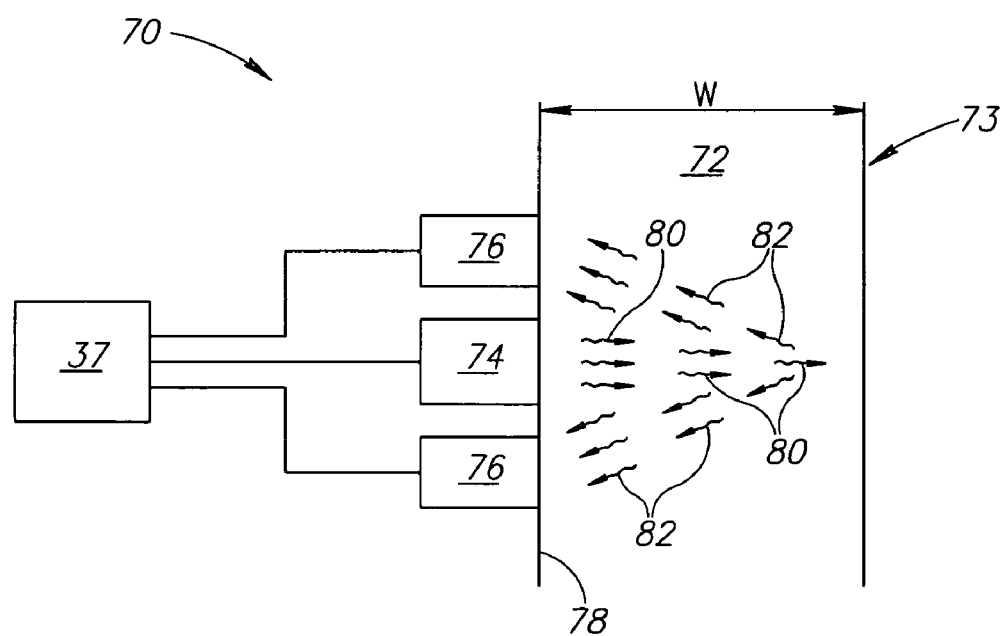
FIG. 3 schematically shows another photometer determining an absorption coefficient for light of a material sample having a thickness substantially greater that an absorption length for the light in the material, in accordance with an embodiment of the present invention.

FIG. 3 schematically shows another photometer 70, in accordance with an embodiment of the present invention. Photometer 70 is shown being used to determine an absorption coefficient of optionally a liquid 72 contained in a suitable receptacle, or, optionally, flowing through a suitable flow cell 73. The width "W" of flow cell 73 is much greater than an absorption length of the liquid for which photometer 70 is determining an absorption coefficient.

Photometer 70 operates similarly to photometers 20 and 60. However, unlike photometers 20 and 60, photometer 70 optionally does not comprise an energy detector that is positioned opposite a light source.

Photometer 70 comprises a light source 74 and at least one acoustic detector 76. By way of example, photometer 70 is shown with two acoustic detectors 76. Both light source 74 and acoustic detectors 76 are optionally positioned in contiguous contact with a same surface 78 of flow cell 73.

As in photometers 20 and 60, to determine an absorption coefficient for liquid 72, light source 74 transmits a pulse of light, represented by wavy arrows 80, that passes through the walls of flow cell 73 and enters the liquid. However, since detectors 76 are not positioned opposite light source 74, they do not receive a pulse of immediate energy from which to generate an immediate signal from light in light pulse 80 that completely traverses liquid 72 directly from the light source to the detectors. Instead, detectors 76 receive a pulse of immediate energy from light that is back scattered by liquid 72 from light pulse 80 towards the detectors and not absorbed by the material. Wavy arrows 82 represent light that is back scattered by liquid 72 from pulse 80.

In accordance with an embodiment of the present invention, detectors 76 generate immediate signals responsive to back scattered light 82. Subsequently, detectors 76 generate delayed signals responsive to delayed energy that reaches the detectors in a pulse of delayed acoustic energy from ultrasound waves generated in a photoacoustic process from energy absorbed by liquid 72 from light pulse 80. It is noted that whereas all detectors 76 shown in FIG. 3 are on a same side of flow cell 73, in some embodiments of the invention, a detector 76 used to generate delayed signals may be located elsewhere. For a detector used to generate delayed signals may be located on a region of flow cell 73 opposite light source 74.

Photometer 70 operates to determine the absorption coefficient of liquid 72 without need to determine an optical path-length in the liquid for light that is used to determine the absorption coefficient. For example, for such a situation, using a very simplified model and assuming single scattering, an amount of immediate energy IE incident on detectors 76 from a light pulse 80 of pulse length "τ" and initial intensity $I_o$ may be written $$IE = \tau \int_0^\infty \int_{2\pi}^{4\pi} I_o \varepsilon(x, \Omega) \sigma(\Omega) \exp(-2\alpha x) dx d\Omega.$$

In the expression for IE, x represents depth into the liquid, $\sigma(\Omega)$ is an elastic scattering cross-section for light as a function of solid angle and $\epsilon(x,\Omega)$ is a "geometrical" collection efficiency of detectors 76 for light back scattered into a solid angle $\Omega$ from a depth x in the material. The factor 2 appears in the argument of the exponential function to account, approximately, for attenuation of light that is back scattered to detectors 76. (A path-length of light back scattered to detectors 76 from a depth x is approximated in the above expression for IE as equal to 2x.) Integration over solid angle is over the "back solid angles", from solid angle $2\pi$ to solid angle $4\pi$, and integration over depth of in the liquid is optionally from 0 to ∞. Integration is performed over the back solid angles because light reaching detectors 76 is back scattered light. Integration over depth x is from 0 to infinity because it is assumed that width of flow cell 73 is much greater than an absorption length, $1/\alpha$, of liquid 72.

Practice of the invention is not limited to any particular theoretical model, such as the simplified model described above, relating IE to an absorption coefficient $\alpha$. In practice, generally a substantially more complicated model and/or numerical methods such as Monte-Carlo and/or inverse Monte Carlo methods may be used to determine IE as a function of $\alpha$. Nor is a model used to process signals generated by detectors 76 limited to details used in the above simple model. For example, whereas integration over depth in liquid 72 in the integrals noted in the above discussion is from 0 to ∞, the limits of integration may be different. An upper limit may be the width of flow tube 73. Optionally, the upper limit is treated as a variable and is determined by a best fit method.

A similar expression for delayed energy DE that reaches detectors 76 may be written $$DE = \tau \int_0^\infty \int_{2\pi}^{4\pi} I_o \varepsilon(x, \Omega) \rho(\alpha \exp(-\alpha x)) dx d\Omega.$$

In the expression for DE, $\tau(\alpha\exp(-\alpha x))$ is an amount of energy absorbed from light pulse 80 per unit volume of the liquid 72 at a depth x, and $\rho$ is a proportionality constant that relates the amount of absorbed energy to intensity of a photoacoustic wave generated in a volume of the liquid that absorbs the energy. (For simplicity it is assumed that $\rho$ is a constant independent of the amount of absorbed energy.) As in the case of determining IE, practice of the invention is not limited to any particular theoretical model, or details of such a model, relating IE to an absorption coefficient $\alpha$. Generally, a model substantially more complicated than the simplified model described above and/or numerical methods such as Monte-Carlo and/or inverse Monte Carlo methods may of course be used to determine DE as a function of $\alpha$.

From the expressions for IE and DE it is seen that IE and DE are independent of path-length of the light pulse in liquid 72. The geometric collection efficiency can be determined from a proper modeling of the geometry of photometer 70 and an assumption regarding scattering of light in the light pulse as a function of depth traveled in the liquid.

However, to determine absorption coefficient α from the above expressions for IE and DE the elastic scattering cross-section for light, $\sigma(\Omega)$, and the photoacoustic coupling coefficient, $\rho$, must be known. In some embodiments of the present invention, $\sigma(\Omega)$ and $\rho$ are estimated from cross-sections and photoacoustic coupling constants that are known for a liquid similar to liquid 72 for which an absorption coefficient is being determined. Furthermore, as in the case of a cuvette noted in the discussion of FIG. 2 above, calibration measurements are optionally performed with a known liquid in flow cell 73 to account for effects of the flow cell on signals generated by detectors 76 responsive to IE and DE.

It is noted that whereas in the discussion above, the equations for IE and DE do not include dependence on time, in some embodiments of the invention, time dependence of signals responsive to EI or DE are used to determine an absorption coefficient for liquid 72. Since immediate energy E is incident on detectors 76 during a relatively short time period substantially equal to the pulse width of pulses provided by light source 74, signals responsive to IE are usually a function substantially only of the pulse width and response time of detectors 76. On the other hand, signals responsive to DE will in general exhibit time dependence responsive to transit times of photoacoustic waves from depths (i.e. x in the equations above) in liquid 72 at which the photoacoustic waves are generated. For example, assume a first liquid 72 having an absorption coefficient at a given wavelength of light that is substantially larger than that of a second liquid 72. A signal responsive to photoacoustic waves (i.e. delayed photoacoustic energy IE), generated in the first liquid 72 by a pulse of light at the given wavelength will have a substantially shorter duration and substantially larger maximum amplitude than a signal responsive to photoacoustic waves generated by an identical pulse in the second liquid 72. The temporal form of the signals responsive to IE and DE in the liquids are optionally used to determine their respective absorption coefficient for light at the given wavelength.

It is further noted that the invention is not limited to the particular configuration of light source and detectors that are shown in FIG. 3. For example, a detector for detecting light scattered from a pulse of light provided by light source 74 may be located along a direction perpendicular to a direction of propagation of the light pulse.

Figure 4:
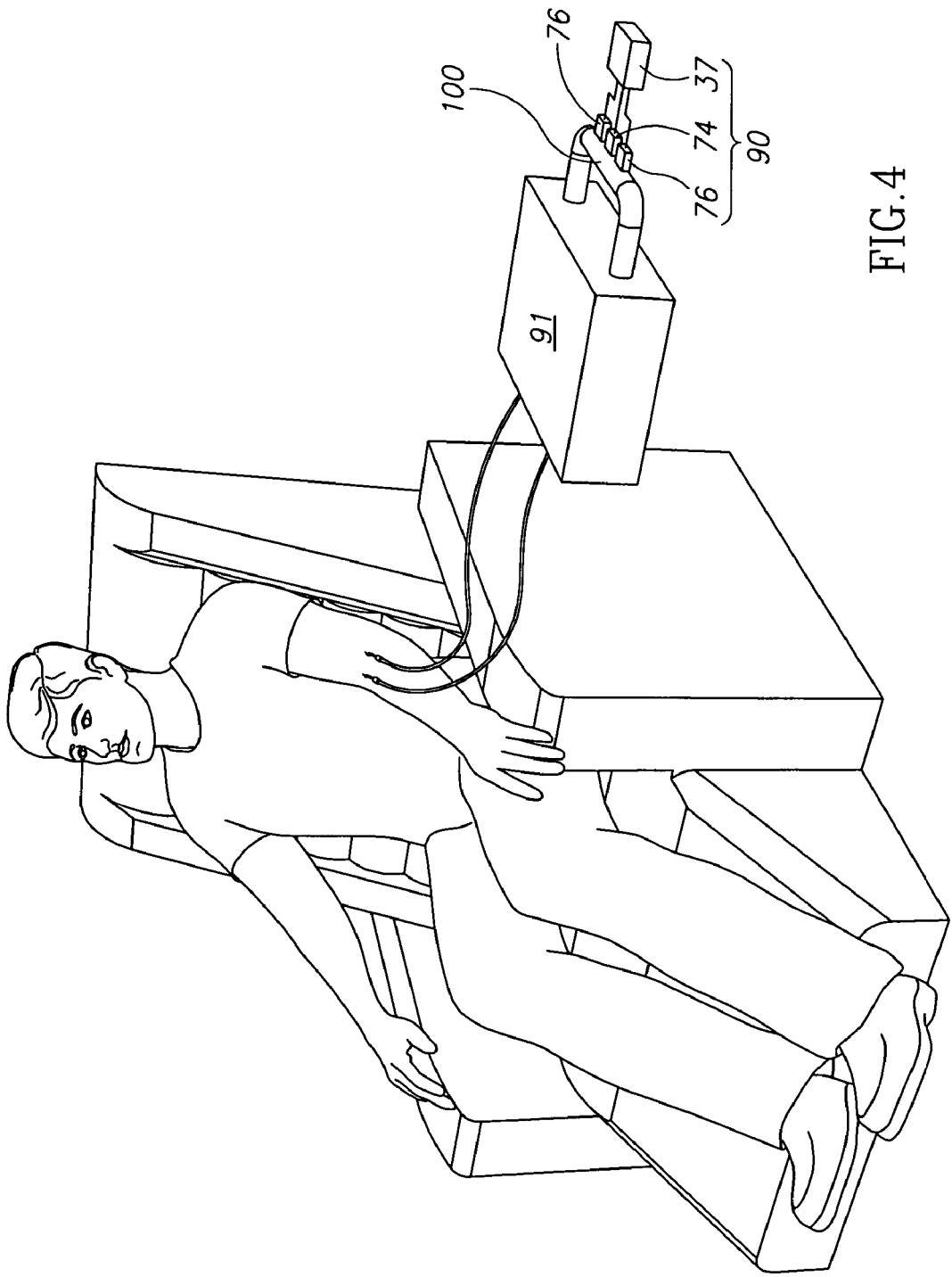
FIG. 4 schematically shows a "medical" photometer, similar to that shown in FIG. 3 being used to acquire ex-vivo measurements of a patient's blood in accordance with an embodiment of the invention.

In some embodiments of the invention, a photometer similar to photometer 70 is used as a medical photometer to acquire optical absorption measurements of blood of a patient. FIG. 4 schematically shows a medical photometer 90, in accordance with an embodiment of the invention, similar to photometer 70 being used to provide absorption measurements of a patient undergoing an operation. Optionally, the absorption measurements are used directly or indirectly, using any of various methods known in the art to determine concentration of an analyte, such as for example glucose or hemoglobin, in the patient's blood.

The patient's blood is schematically shown being withdrawn from and recirculated into the patient's vascular system during a medical procedure by a suitable apparatus 91 for performing the procedure. Apparatus 91 may, for example, be a dialysis machine. In accordance with an embodiment of the invention, apparatus 91 directs the blood it withdraws from the patient's vascular system, or shunts a portion thereof, through a flow cell 100 comprised in medical photometer 90. Flow cell 100 is coupled to a light source 74 and at least one detector 76 for performing optical measurements of blood passing through the flow cell, in accordance with an embodiment of the invention. Optionally, a dimension of the cross-section of flow cell 100 along which light source 74 transmits light into the flow cell to acquire optical measurements of blood has a length that is greater than the absorption length of the light in the blood. Optionally the cross-section dimension is greater than two absorption lengths. Optionally, the cross-section dimension is greater than five absorption lengths. Optionally, the cross-section dimension is greater than ten absorption lengths.

The light source and at least one detector optionally operate similarly to the manner in which light source 74 and at least one detector 76 comprised in photometer 70 shown in FIG. 3 operate. A controller 37 optionally determines IE, DE and an absorption coefficient for light at at least one wavelength provided by light source 74. Optionally, controller 37 assays an analyte in the blood circulated by medical apparatus 91 responsive to the signals provided by at least one detector 76. Assuming a distance between walls of flow cell 100 is known, a time between acoustic delayed energy pulses repeatedly reflected back and forth between the walls is used to determine a speed of sound in the blood and the determined speed of sound is optionally used to determine an absorption coefficient and/or an assay.

Whereas, photometer 90 determines an absorption coefficient and/or an assay responsive to immediate and delayed signals IS and DS provided by at least one detector 76, in some embodiments of the invention, a photometer, optionally similar to photometer 90, determines an absorption coefficient and/or assay for blood without recourse to a measure of immediate energy. Optionally, the photometer comprises a detector that provides signals responsive to intensity of light provided by light source 74 and controller 37 determines intensity of light from signals provided by the detector. The controller uses the delayed signals DS provided by at least one detector 76 and the determined intensity to determine the absorption coefficient and/or assay.

In some embodiments of the invention, a photometer similar to photometer 90 determines an absorption coefficient and/or scattering coefficient using the amplitude, and/or slope, and/or temporal shape of signals generated by at least one detector 76 responsive to photoacoustic waves that light from light source 74 stimulates in blood in flow cell 100. Optionally, the signals are processed to determine the absorption and/or scattering coefficient using methods described in an article by A. A. Oraevsky et al entitled "Determination of Tissue Optical Properties by Piezoelectric Detection of Laser-Induced Stress Waves"; SPIE Vol. 1882 Laser-Tissue Interaction IV (1993); pp 86-98.

It is noted that whereas in FIG. 4 photometer 90 is shown as a component of a larger apparatus 91, in some embodiment of the invention, a photometer in accordance with an embodiment of the invention, is a "stand alone" monitor that is not comprised in a larger system. The photometer comprises its own pump for circulating blood from a person's body through a flow cell. Optionally, the photometer pumps blood out from the person's body along a first direction in a suitable conduit and back into the body in an opposite direction in the same conduit using method known in the art.

In the above discussion, energy detectors used to detect immediate energy IE and delayed energy DE have been assumed to be acoustic detectors. Photometers, in accordance with some embodiments of the present invention, comprise in place of acoustic detectors, energy detectors that are thermal detectors that generate signals responsive to thermal energy that they receive. Components and configurations of photometers, in accordance with embodiments of the present invention, that comprise thermal detectors are similar to configurations of photometers that comprise acoustic detectors, in accordance with embodiments of the present invention, with the acoustic detectors replaced with thermal detectors. A "thermal photometer", in accordance with an embodiment of the present invention operates similarly to the manner in which a corresponding "acoustic photometer" operates.

When a light pulse from a light source in a thermal photometer is transmitted through or reflected from a material for which an absorption coefficient is to be determined, at least some of the light in the light pulse that is not absorbed by the material is incident on a thermal detector that the photometer comprises. The incident light heats the thermal detector, transmitting immediate energy to the thermal detector in the form of thermal energy. The thermal detector generates an immediate signal IS responsive to the immediate thermal energy. Light from the light pulse that is absorbed by the material heats the material. Thermal energy from regions of the material heated by the light pulse propagates away from the region by convection and is incident on the thermal detector as delayed energy, responsive to which the thermal detector generates a delayed signal DS. In accordance with an embodiment of the present invention, the immediate and delayed signals provided by the thermal detector are used to determine an absorption ratio from which an absorption coefficient of the material is determined.

It is to be noted that whereas in the above examples of photometers in accordance with embodiments of the present invention, a same detector is used to sense immediate energy and delayed energy, in some embodiments of the present invention different detectors are used to sense immediate and delayed energy. For example, a first detector that senses immediate energy might be positioned, as shown in FIGS. 1-3, i.e. opposite or adjacent to a light source that radiates a light pulse into a material whose absorption coefficient is being measured. A second detector that senses delayed energy might be located on a surface of the material that is substantially parallel to a direction along which the light source radiates the light pulse. (It is noted that delayed energy is generally emitted substantially isotropically by a region of the material that absorbs energy from a light pulse transmitted into the material. As a result, a position for a second detector that senses delayed energy other than positions shown in FIGS. 1-3, for example as noted above on a surface parallel to a direction along which the light pulse propagates, is possible and can be advantageous.)

Furthermore, by using different detectors for sensing immediate and delayed energy, in accordance with an embodiment of the present invention, detectors used to sense immediate energy can be optimized to sense optical energy (i.e. suitable optical detectors), whereas detectors used to sense delayed energy can be optimized to detect a particular desired form of delayed energy, e.g. acoustic or thermal.

It is further noted that in some embodiments of the present invention, delayed energy as well as immediate energy may be optical energy. For example, optical energy absorbed from a light pulse by a sample whose absorption coefficient is being measured, in accordance with an embodiment of the present invention, may cause the sample material to luminesce following a release delay. The luminesced light is sensed and used to determine the amount of delayed energy. Generally, the luminesced light is characterized by a wavelength that is different than the wavelength of the light that characterizes the light pulse from which the optical energy is absorbed. As a result, light proportional to immediate energy may be distinguished, in accordance with an embodiment of the present invention, from luminesced light proportional to delayed energy not only by temporal separation (i.e. by absorption delay) but also by difference in wavelength.

In the description and claims of the present application, each of the verbs, "comprise," "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. The scope of the invention is limited only by the following claims.

The invention claimed is:

1. A method of determining an optical parameter or function thereof for blood ex-vivo, the method comprising:
   withdrawing blood from a patient's vascular system;
   flowing the blood through a flow cell ex-vivo;
   transmitting a pulse of light into the blood in the flow cell as the blood flows through said flow cell, wherein transmitting the light in a direction along which the internal cross-section of the flow cell has a dimension that is greater than an absorption length of the light in the blood;
   generating a signal responsive to energy that the material emits responsive to a portion of the light from the light pulse that is absorbed by the blood using the signal to determine the optical parameter or function thereof; and
   recirculating the blood into the patient's vascular system.

2. A method according to claim 1 wherein the dimension is greater than two absorption lengths of the light in the blood.

3. A method according to claim 1 wherein the dimension is greater than five times the absorption length.

4. A method according to claim 1 wherein the dimension is greater than ten times the absorption length.

5. A method according to claim 1 wherein the energy that the blood emits is acoustic energy generated by a photoacoustic effect.

6. A method according to claim 1 wherein the energy that the blood emits is thermal energy.

7. A method according to claim 1 and comprising generating a signal responsive to light from the light pulse that is scattered by the blood and using the signal to determine the optical parameter or function thereof.

8. A method according to claim 1 and comprising:
   receiving light scattered by the blood from the light pulse;
   generating a signal responsive to the received scattered light;
   providing a model that relates the received scattered light to a distance that the light travels in the blood;
   assuming a value for the distance; and
   determining the optical parameter or function thereof responsive to the signal, the model and the assumed value.

9. A method according to claim 8 wherein the assumed distance is infinite.

10. A method according to claim 8 wherein the assumed distance is substantially greater than an absorption length of the light in the material.

11. A method according to claim 8 wherein the optical parameter comprises an absorption coefficient for the light.

* * * * *

UNITED STATES PATENT AND TRADEMARK OFFICE
CERTIFICATE OF CORRECTION

PATENT NO. : 7,646,484 B2
APPLICATION NO. : 11/355434
DATED : January 12, 2010
INVENTOR(S) : Pesach et al.

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by (261) days Delete the phrase "by 261 days" and insert -- by 500 days --

Signed and Sealed this

Fourth Day of May, 2010

David J. Kappos
*Director of the United States Patent and Trademark Office*